United States Patent
Kashiwagi et al.

(10) Patent No.: US 8,294,889 B2
(45) Date of Patent: Oct. 23, 2012

(54) METHOD FOR INSPECTING NANO-IMPRINT TEMPLATE

(75) Inventors: Hiroyuki Kashiwagi, Fujisawa (JP);
Kazuya Fukuhara, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 250 days.

(21) Appl. No.: 12/776,003

(22) Filed: May 7, 2010

(65) Prior Publication Data
US 2010/0315643 A1 Dec. 16, 2010

(30) Foreign Application Priority Data
Jun. 10, 2009 (JP) .................................. 2009-139275

(51) Int. Cl.
*G01N 21/01* (2006.01)

(52) U.S. Cl. .................................. 356/237.2; 356/237.5
(58) Field of Classification Search .... 356/237.1–237.5, 356/364
See application file for complete search history.

(56) References Cited

U.S. PATENT DOCUMENTS

| | | | | |
|---|---|---|---|---|
| 5,288,996 A * | 2/1994 | Betzig et al. | ............. | 250/227.26 |
| 5,333,495 A * | 8/1994 | Yamaguchi et al. | ............ | 73/105 |
| 5,894,349 A * | 4/1999 | Harris et al. | ................... | 356/632 |
| 7,586,606 B2 * | 9/2009 | Inoue et al. | ................... | 356/364 |
| 7,815,824 B2 * | 10/2010 | Sreenivasan et al. | ........ | 264/40.1 |
| 2003/0203502 A1 * | 10/2003 | Zenhausern et al. | .......... | 436/164 |
| 2003/0205658 A1 * | 11/2003 | Voisin | ........................ | 249/187.1 |
| 2006/0006317 A1 * | 1/2006 | Itoh et al. | ................. | 250/227.11 |
| 2009/0315223 A1 * | 12/2009 | Yoneda et al. | ................ | 264/402 |
| 2010/0091294 A1 * | 4/2010 | Kim et al. | ..................... | 356/491 |
| 2011/0043795 A1 * | 2/2011 | Den Boef et al. | .......... | 356/237.2 |
| 2011/0129930 A1 * | 6/2011 | Wuister | .......................... | 436/35 |

FOREIGN PATENT DOCUMENTS
JP 2000-164663 6/2000
* cited by examiner

*Primary Examiner* — Hoa Pham
(74) *Attorney, Agent, or Firm* — Finnegan, Henderson, Farabow, Garrett & Dunner, L.L.P.

(57) ABSTRACT

A method for inspecting a nano-imprint template, includes irradiating light onto a template for nano-imprinting from a back surface side of the template, the template having a front surface where a pattern is formed, detecting near-field light which is generated near the front surface of the template by the irradiation of the light, and performing an inspection of the template on the basis of the detected near-field light.

7 Claims, 5 Drawing Sheets

METHOD FOR INSPECTING NANO-IMPRINT TEMPLATE

CROSS-REFERENCE TO RELATED APPLICATIONS

This application is based upon and claims the benefit of priority from prior Japanese Patent Application No. 2009-139275, filed Jun. 10, 2009, the entire contents of which are incorporated herein by reference.

BACKGROUND OF THE INVENTION

1. Field of the Invention

The present invention relates to a method for inspecting a nano-imprint template.

2. Description of the Related Art

With recent miniaturization of nano-imprint templates, demands have arisen for a method for inspecting templates with high accuracy. Where an optical inspection method is considered as such a method for inspecting templates, inspection resolution is limited by a diffraction limit, and sufficiently smaller defects than wavelengths are therefore difficult to detect.

A technique for enclosing light within a region smaller than a wavelength thereof has been proposed as a method for detecting defects in a semiconductor device comprising a minite pattern (for example, see Jpn. Pat. Appln. KOKAI Publication No. 2000-164663). According to the method described in this publication, electron-hole pairs are generated, and photoexcitation is observed. For a nano-imprint template made of a non-conductive material which does not allow an electric current to flow, however, defects are difficult to detect depending on changes in a minute electric current.

Thus, a method capable of accurately inspecting a template comprising a micro pattern is said to have not been actually proposed yet.

BRIEF SUMMARY OF THE INVENTION

According to an aspect of the present invention, there is provided a method for inspecting a nano-imprint template, comprising: irradiating light onto a template for nano-imprinting from a back surface side of the template, the template having a front surface where a pattern is formed; detecting near-field light which is generated near the front surface of the template by the irradiation of the light; and performing an inspection of the template on the basis of the detected near-field light.

DETAILED DESCRIPTION OF THE INVENTION

Hereinafter, embodiments of the invention will be described with reference to the drawings.

First Embodiment

Figure 1:
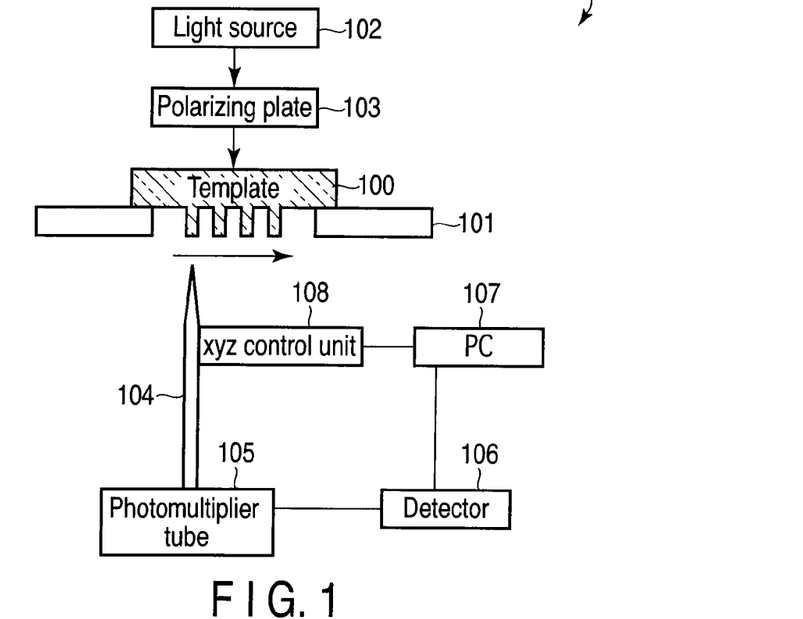
FIG. 1 schematically illustrates a basic configuration of a device for inspecting a nano-imprint template, according to embodiments of the invention.
Figure 2:
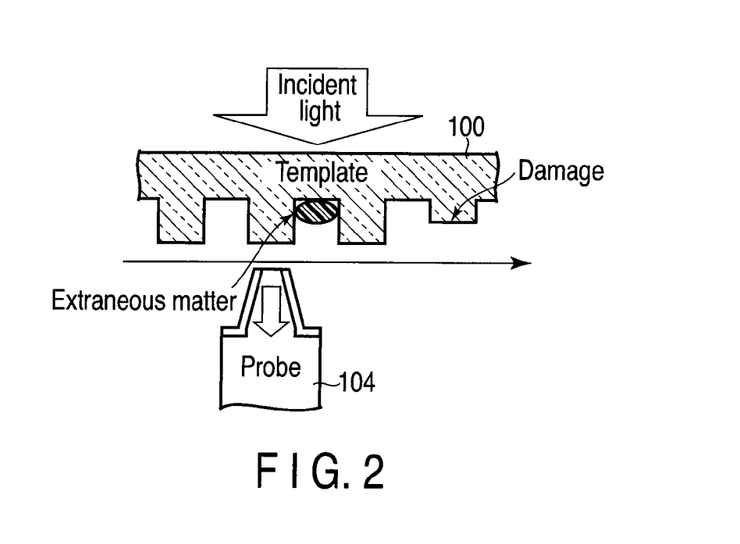
FIG. 2 schematically illustrates a part of a basic configuration of the device for inspecting a nano-imprint template, according to the embodiments of the invention.

Referring to FIGS. 1 and 2, a description will now be made of a method for inspecting a nano-imprint template, according to the first embodiment of the invention.

FIGS. 1 and 2 schematically illustrate a basic configuration of a device for inspecting a nano-imprint template, according to the embodiment of the invention.

As illustrated in FIG. 1, a device 1 for inspecting a nano-imprint template comprises: a jig unit 101 which fixes a template 100 as a target to be inspected; a light source unit 102 which irradiates a back surface of the template 100 with light; a polarizing plate 103 provided between the jig unit 101 and the light source unit 102; a probe 104 which observes near-field light generated in a front surface side (i.e., the side where a pattern is formed) of the template 100; a photomultiplier tube 105 which amplifiers photoelectrons observed by the probe 104; a detector 106 which detects photoelectrons amplified by the photomultiplier tube 105; a PC 107 which records information of the near-field light detected by the detector 106 and derives a relationship between intensity of the near-field light and position of the template, based on a near-field light signal detected by the detector 106; and an xyz control unit 108 which is connected, for example, to the probe 104 and PC 107 and controls the position of the probe 104.

The template 100 is made of a non-conducting material, and a cyclic line-and-space (L/S) pattern is formed in the front surface side of the template 100. Further, the L/S pattern has a sufficiently smaller pitch (for example, about 40 to 60 nm) compared with a wavelength of light supplied from the light source unit 102. The probe 104 is, for example, a fiber probe prepared by sharply tapering a top end of an optical fiber. The probe 104 comprises a top end having a radius of curvature of nanometer order, and a minute opening provided near the top end and having a sufficiently smaller radius of curvature than the wavelength of light so that light other than near-field light may not enter into the probe 104.

Described next will be a specific method for inspecting a template, using the device 1 for inspecting a nano-imprint template.

At first, the template 100 to be inspected is set on and fixed to the jig unit 101. Further, light is generated by the light source unit 102 and is irradiated onto the template 100 through the polarizing plate 103 from the back surface side of the template 100. Owing to irradiation of the light, near-field light is generated in the front surface side of the template 100.

Next, the xyz control unit 108 adjusts the height of the probe 104 (in the Z-direction) to come close to the front surface of the template 100, and moves the probe 104 in the X- and Y-directions along the front surface of the template 100. As the probe 104 is moved close to a region where the near-field light is generated, a top end of the probe 104 receives the near-field light and generates scattered light to become a near-field light signal. Further, the near-field light signal (scattered-light signal) is amplified by the photomultiplier tube 105 connected to the probe 104, and is detected by the detector 106.

Further, the PC 107 derives a relationship between intensity of the near-field light and position of the template, based on the near-field light signal detected by the detector 106. In this manner, intensity distribution of the near-field light generated near the front surface of the template 100 is obtained.

On the template 100, a cyclic L/S pattern is formed. Therefore, if an ideal L/S pattern is formed, cyclicity can be confirmed from intensity distribution of near-field light. However, if the template 100 is clogged with extraneous matter (such as resist), as illustrated in FIG. 2, or if there is a defect such as damage to the template, a change occurs in absolute value or cyclicity of intensity of near-field light. Therefore, if a change in absolute value or cyclicity of intensity of near-field light is observed in a L/S pattern forming region, a defect is found to be present in a portion where the change is observed.

If a defect is thus found in the template 100, i.e., if the absolute value of intensity of near-field light changes or the cyclicity of intensity of near-field light changes, there is a possibility that the template 100 is clogged with resist, and the template 100 is therefore cleaned. Further, near-field light of the template 100 is measured again. If a change occurs in absolute value or cycle of intensity of near-field light in this remeasurement, a defect such as damage exits in the template 100 with high possibility, and the template 100 is therefore discarded.

According to the first embodiment described above, light is irradiated onto the template 100 from the back surface side of the template 100, and near-field light generated thereby in the front surface side of the template 100 is measured by using the probe 104. Further, intensity of the near-field light is derived based on information detected by the probe 104 with use of the PC 107. Near-field light is non-propagating light which is generated in a region of nanometer order. Further, resolution of nanometer order is achieved by using the probe 104. Whether clogging resist or a defect such as damage is present in a template having a pattern of nanometer order whose pitch is less than a wavelength of light or not can be determined by referring to distribution of the intensity of the near-field light. Therefore, a portion where a defect exits can be accurately specified even on a pattern having a pitch of nanometer order. Accordingly, not only presence or absence of a defect can be determined but also the portion having the defect can be accurately specified. As a result, defects can be prevented from occurring in devices actually formed by transferring the pattern of the template, and manufacturing yield can accordingly improve to thereby reduce manufacturing costs.

Second Embodiment

According to the method of inspection in the first embodiment, presence or absence of a defect in a template 100 and the portion having the defect are specified by referring to a change in absolute value or cyclicity of intensity of near-field light which is generated in the front surface side of the template 100. In the second embodiment, however, a description will be made of a method for specifying presence or absence of a defect in a template 100 and the portion having the defect, by comparing a measurement result of measuring near-field light by use of a reference template 200 which is not defective, with a measurement result of measuring near-field light generated in the front surface side of the template 100.

A method for inspecting a nano-imprint template, according to the second embodiment, will now be described below with reference to FIGS. 1 and 3. Basis of a structure and an inspection method according to the second embodiment is the same as that of the first embodiment. Therefore, components which have been described in the above first embodiment and matters easily derivable from the first embodiment will be omitted from descriptions given below.

Figure 3:
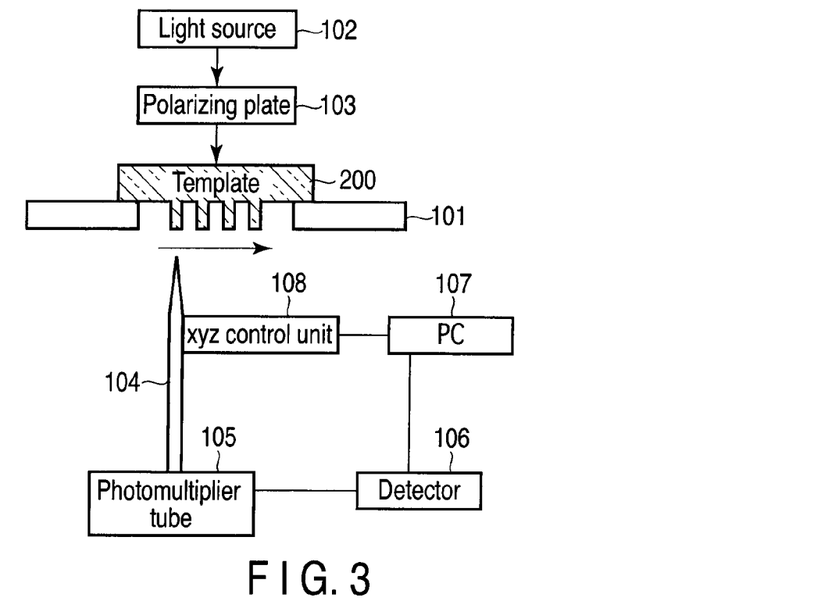
FIG. 3 schematically illustrates a basic configuration of a device for inspecting a nano-imprint template, according to the embodiments of the invention.

FIGS. 1 and 3 schematically illustrate a basic configuration of a device for inspecting a nano-imprint template, according to the embodiments of the invention.

At first, to derive ideal intensity distribution of near-field light, near-field light is measured by using an ideal template 200 which is not defective (namely, a reference template 200). The reference template 200 has the same configuration as the template 100. A method for selecting the reference template 200 is, for example, to determine presence or absence of a defect by actually transferring a pattern actually formed in a template and by further observing the transferred pattern with a SEM. If a template is determined not to be defective, the template is selected as the reference template 200. By performing a process with use of the reference template 200, the reference template 200 becomes a used template 100. As illustrated in FIG. 3, the reference template 200 is set on and fixed to a jig unit 101. Further, light is generated by a light source unit 102, and is irradiated onto the reference template 200 from the back surface side of the reference template 200 through a polarizing plate 103.

Next, the xyz control unit 108 adjusts a probe 104 in the Z-direction to come close to the surface of the reference template 200, and moves the probe 104 in the X- and Y-directions along the surface of the reference template 200. As the probe 104 is moved close to a region where the near-field light is generated, a top end of the probe 104 generates scattered light to become a near-field light signal. Further, the near-field light signal (namely, scattered-light signal) is amplified by a photomultiplier tube 105 connected to the probe 104, and is detected by a detector 106.

Further, a PC 107 derives a relationship between intensity of the near-field light and position of the template, based on the near-field light signal detected by the detector 106. In this manner, intensity distribution of near-field light generated near the surface of the template 100 is obtained. This intensity distribution of near-field is recorded as ideal intensity distribution of near-field light in the PC 107.

Next, as illustrated in FIG. 1, a used template 100 is set on and fixed to the jig unit 101. Light is then generated by the light source unit 102 and is irradiated onto the template 100 from the back surface side of the template 100 through the polarizing plate 103.

Next, the probe 104 is adjusted in the Z-direction, and is moved in the X- and Y-directions along the front surface of the template 100. As the probe 104 is moved close to a region where the near-field light is generated, a top end of the probe 104 generates a near-field light signal. Further, the near-field light signal is detected by the detector 106 through the photomultiplier tube 105 connected to the probe 104.

Further, the PC 107 derives a relationship between intensity of the near-field light and position of the template, based on the near-field light signal detected by the detector 106. In this manner, intensity distribution of the near-field light generated near the surface of the template 100 is obtained.

Next, the PC 107 compares ideal intensity distribution of near-field light with the intensity distribution of the near-field light which has been obtained from the template 100. If no change in absolute value or cyclicity of the intensity of the near-field light is found, the template 100 is determined to include neither clogging resist nor a defect such as damage to the template. Otherwise, if a change in absolute value or cyclicity of the intensity of the near-field light is found, a defect is determined to be present in a portion where the change is observed.

If a defect is thus found, i.e., if a change occurs in absolute value or cyclicity of the intensity of near-field light, the template 100 is cleaned. Further, near-field light is measured again. If a change still occurs in absolute value or cycle of intensity of the near-field light of the template 100, the template 100 is discarded.

According to the second embodiment described above, light is irradiated onto the reference template 200 which is not defective from the back surface side of the reference template 200, and near-field light generated thereby in the front surface side of the reference template 200 is measured by using the probe 104. Further, ideal intensity distribution of near-field light is derived with use of the PC 107, based on information detected by the probe 104. Further, as in the first embodiment described previously, light is irradiated onto a template 100 as a measurement target from the back surface side of the template 100, and near-field light generated thereby in the front surface side of the template 100 is measured by using the probe 104. Further, intensity distribution of the near-field light is derived based on information detected by the probe 104 with use of the PC 107. Thereafter, a result of measuring the near-field light using the reference template 200 which is not defective is compared with a result of measuring the near-field light detected from the template 100. Even for a template having a pattern of nanometer order whose pitch is less than a wavelength of light, presence or absence of a defect and the portion having the defect can be accurately specified by referring to near-field light. As a result, defects can be prevented from occurring in devices actually formed by transferring a pattern of a template, and manufacturing yield can be accordingly improved to thereby reduce manufacturing costs.

Third Embodiment

According to the method for inspection in the first embodiment, presence or absence of a defect in a template 100 and the portion having the defect are specified by referring to changes in absolute value or cyclicity of intensity of near-field light generated in the front surface side of the template 100. In the third embodiment, a description will be made of a method in which presence or absence of a defect in a template 100, and the portion having the defect and the type of the defect are specified by estimating near-field light through a simulation using design data of the template 100, and by comparing a measurement result of measuring near-field light actually detected from the template 100, with a result of the simulation.

A method for inspecting a nano-imprint template, according to the third embodiment, will now be described below with reference to FIGS. 4, 5A, 5B, 6A, 6B, 7A, and 7B. Basis of a structure and an inspection method of the third embodiment is the same as that of the first embodiment. Therefore, components which have been described in the above first embodiment and matters derivable easily from the first embodiment will be omitted from descriptions given below.

Figure 4:
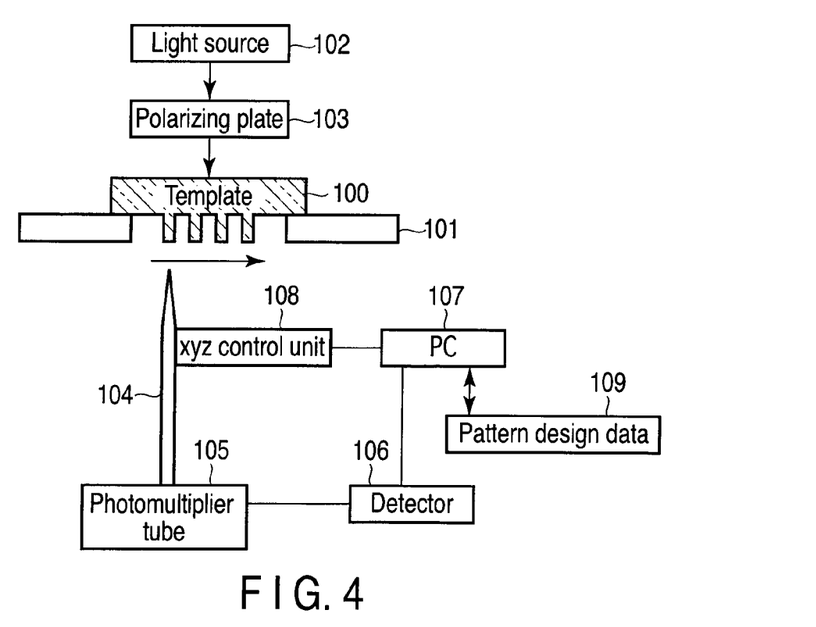
FIG. 4 schematically illustrates a basic configuration of an inspection device for nano-imprint templates, according to an embodiment of the invention.

FIG. 4 schematically illustrates a basic configuration of a device for inspecting a nano-imprint template, according to this embodiment of the invention.

As illustrated in FIG. 4, a template 100 is set on and fixed to a jig unit 101. Further, light is generated by a light source unit 102 and is irradiated onto the template 100 through a polarizing plate 103 from the back surface side of the template 100.

Next, an xyz control unit 108 adjusts a probe 104 in the Z-direction to come close to the front surface of the template 100, and moves the probe 104 in the X- and Y-directions along the surface of the template 100. As the probe 104 is moved close to a region where the near-field light is generated, a top end of the probe 104 generates scattered light to become a near-field light signal. Further, the near-field light signal is amplified by a photomultiplier tube 105 connected to the probe 104, and is detected by a detector 106.

Further, a PC 107 derives a relationship between intensity of the near-field light and position of the template, based on the near-field light signal detected by the detector 106. In this manner, intensity distribution of the near-field light generated near the front surface of the template 100 is obtained.

In the third embodiment, the PC 107 obtains design data of the template 100 from pattern design data 109, and performs a simulation of near-field light measurement in advance.

A simulation method using the design data of the template 100 will now be schematically described with reference to FIGS. 5A, 5B, 6A, 6B, 7A, and 7B.

Figure 5A:
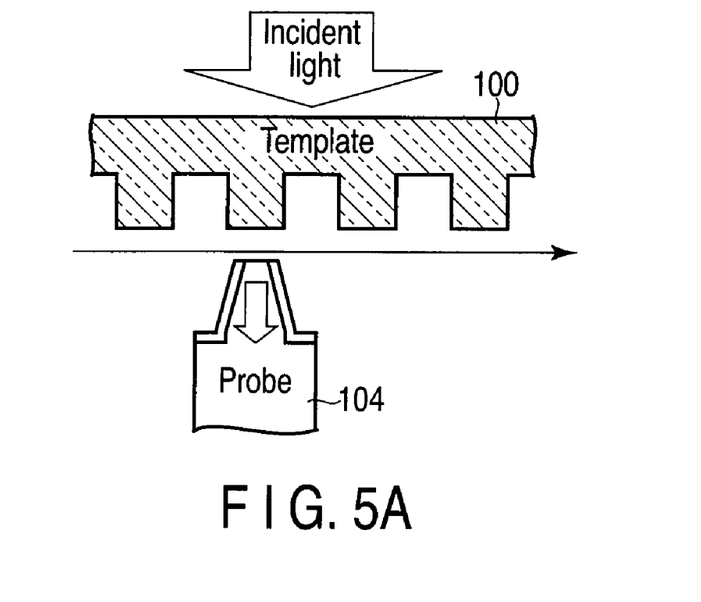
FIG. 5A illustrates a setting for a template when performing a simulation using design data of a nano-imprint template.
Figure 5B:
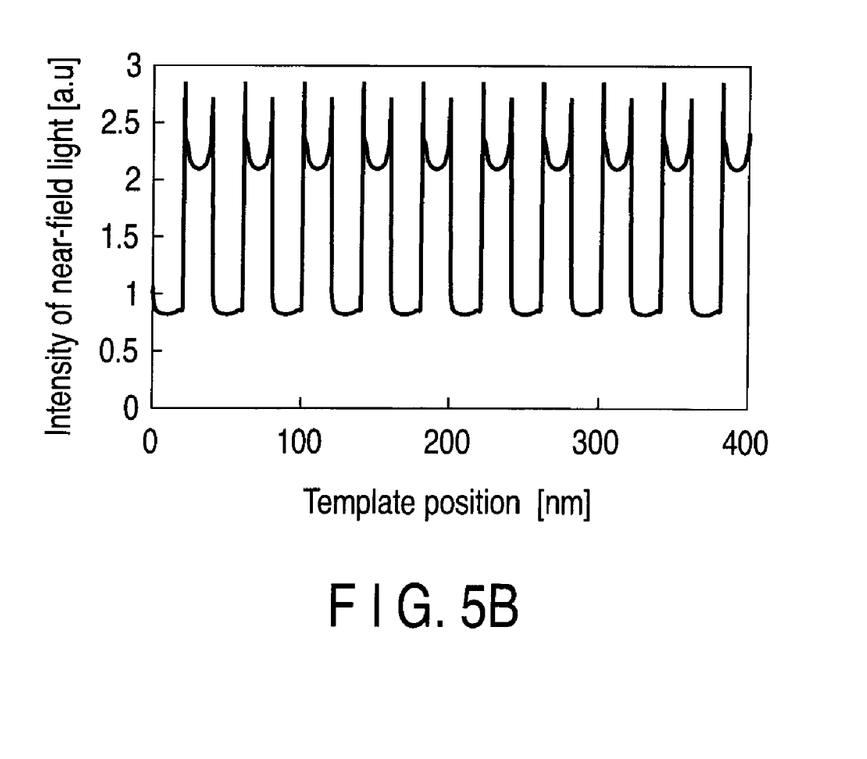
FIG. 5B is a graph representing intensity distribution of near-field light generated near a front surface of the template, which is calculated by performing the simulation using the design data of the nano-imprint template.
Figure 6A:
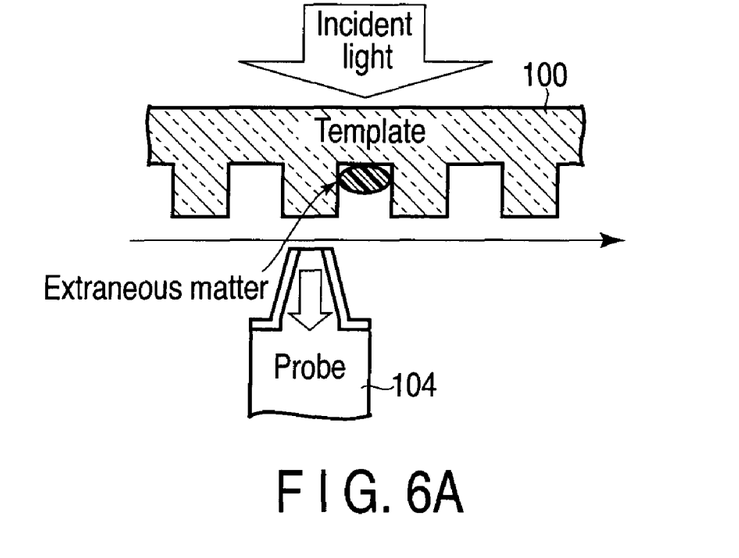
FIG. 6A illustrates a setting for a template when performing a simulation using design data of a nano-imprint template.
Figure 6B:
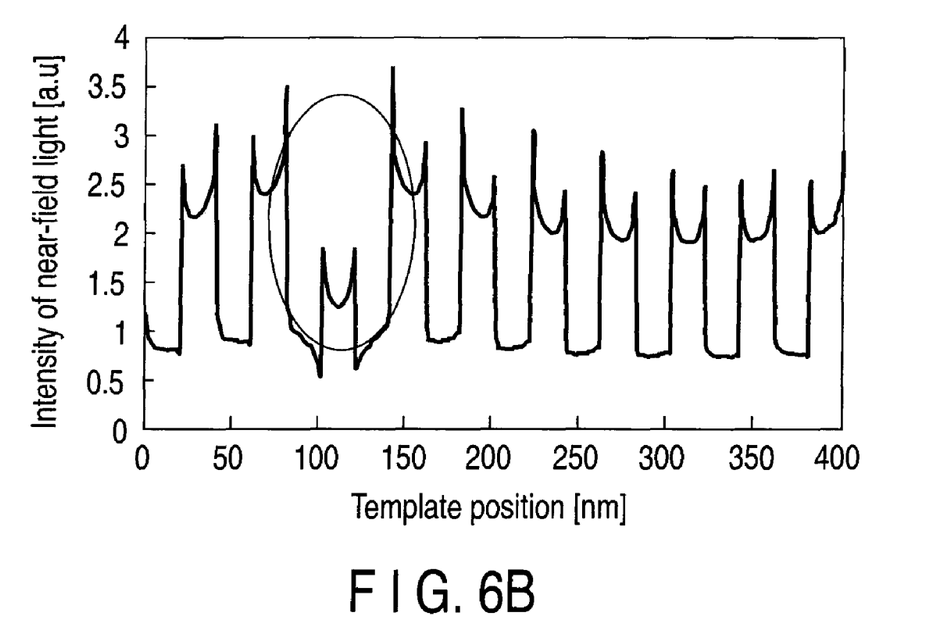
FIG. 6B is a graph representing intensity distribution of near-field light generated near a front surface of the template, which is calculated by performing the simulation using the design data of the nano-imprint template.
Figure 7A:
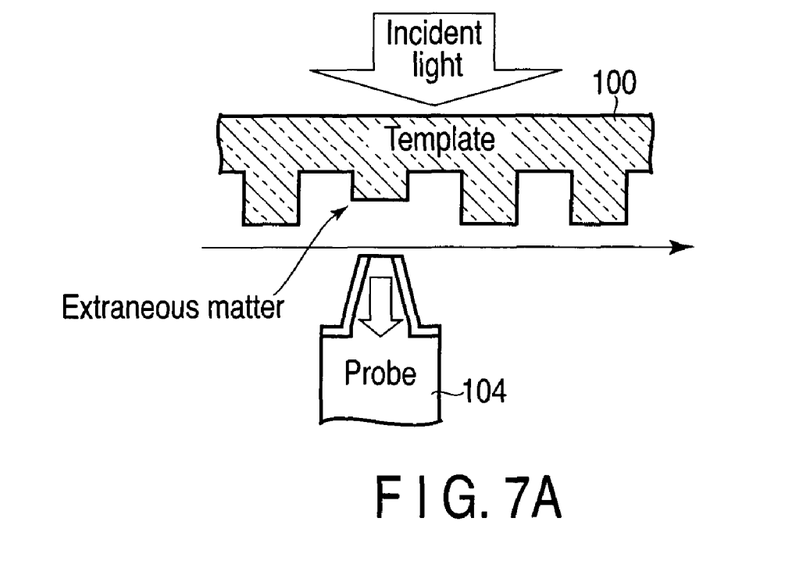
FIG. 7A illustrates a setting for a template when performing a simulation using design data of a nano-imprint template.
Figure 7B:
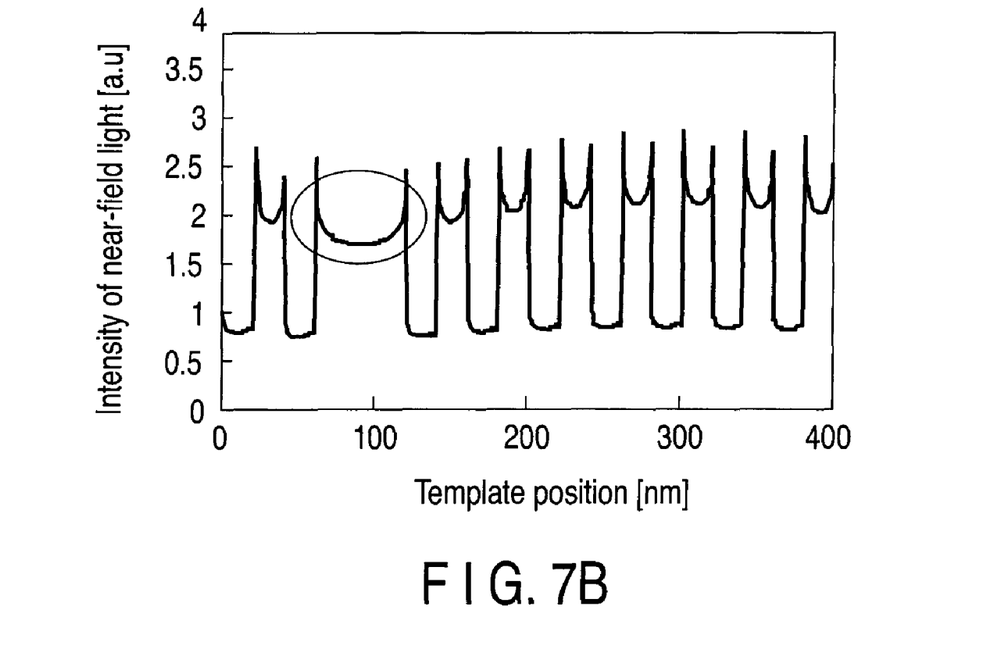
FIG. 7B is a graph representing intensity distribution of near-field light generated near a front surface of the template, which is calculated by performing the simulation using the design data of the nano-imprint template.

FIGS. 5A, 6A and 7A illustrate settings for a template where a simulation is performed by using design data of a nano-imprint template. FIGS. 5B, 6B and 7B are graphs representing intensity distribution of near-field light generated near the front surface of a template, wherein the intensity distribution is calculated by performing the simulation with use of the design data of the nano-imprint template. In each of the graphs in FIGS. 5B, 6B and 7B, the horizontal axis represents position of the template, and the vertical axis represents intensity of near-field light.

As in FIGS. 5A and 5B, if the template 100 having a cyclic L/S pattern contains no defect, intensity distribution of near-field light is obtained in accordance with cyclicity of the L/S pattern. This simulation data is taken as reference intensity distribution of near-field light.

FIGS. 6A and 6B represent a simulation result when a part of a L/S pattern is clogged with a minute quantity of material (such as resist) different from the material forming the template 100. In this case, the absolute value of intensity of near-field light is found to locally decrease at a position corresponding to template coordinates of 100 to 120 nm, compared with intensity of near-field light in the periphery of this position. These coordinates correspond to a position where the template 100 is clogged with extraneous matter having a width of 20 nm or so. If such an intensity distribution is obtained, clogging by a minute quantity of material is assumed to be occurring. Near-field light depends on the polarization of a substance regardless of the spatial phase and wavelength of light. Therefore, a near-field light signal excited by the template is considered to reflect the difference between the material forming the template and the extraneous matter causing the clogging. Accordingly, not only a defective portion but also the type of matter causing the clogging can be estimated.

FIGS. 7A and 7B represent a simulation result when the L/S pattern is partially damaged. In this case, intensity distribution of near-field light at a position corresponding to template coordinates of 60 to 120 nm is 40 nm wider than the periphery of these template coordinates. A damaged template causes disturbance in cyclicity of the L/S pattern, which is considered to change width (cycle) of near-field light. As a result, not only a defective portion of a nano-meter scale is extracted but also cyclicity is determined to be abnormal. Accordingly, damage to the template can be estimated.

Therefore, ideal intensity distribution of near-field light as represented in FIGS. 5A and 5B is stored in advance, and characteristics of intensity distribution of near-field light corresponding respectively to types of defects as described with reference to FIGS. 6A, 6B, 7A, and 7B are also stored as information in advance.

Further, the PC 107 compares the intensity distribution of near-field light based on a simulation result obtained as described above, with intensity distribution of near-field light of the template 100 actually derived through process in FIG. 4. As illustrated in FIG. 5B, if there is not particularly a change in the actually derived intensity distribution of near-field light, the template 100 is determined not to be defective. Otherwise, if there is a change in the actually derived intensity distribution of near-field light, the template 100 is determined to be defective.

If the template 100 is determined to be defective and if a change in absolute value of intensity in the intensity distribution of near-field light of the template 100 is found, the pattern is determined to be clogged with resist at the position where the change is found. If the pattern is determined to be clogged with resist, the template 100 is cleaned. Further, how the pattern is clogged and the substance causing the clogging can be determined depending on the polarization of the substance causing the clogging. Hence, whether the substance can be removed by cleaning or not can be determined. Furthermore, if a change is found in cyclicity of intensity distribution of near-field light of the template 100, damage is determined to be present in the template in the portion where the change is found. If damage is thus found in the template, the template 100 is discarded.

According to the third embodiment described above, a simulation is performed in advance with use of design data of a template 100. In this manner, intensity distribution of near-field light for an ideal template is estimated, and variations of intensity distribution of near-field light corresponding to various conditions of the template can be estimated. Accordingly, characteristics of distribution depending on types of defects can be determined. Besides, as in the first embodiment described above, light is irradiated onto the template 100 from the back surface side of the template 100, and near-field light generated thereby in the front surface side of the template 100 is measured by using the probe 104. Further, intensity distribution of the near-field light is derived based on information detected by the probe 104. The type of a defect in the template 100 and the portion having the defect are accurately determined by comparing the estimated intensity distribution of near-field light with intensity distribution of the actually measured near-field light of the template 100. Even for a template having a pattern of nanometer order whose pitch is less than a wavelength of light, presence or absence of a defect, the portion having the defect, and the type thereof can be accurately specified by referring to near-field light. As a result, defects can be prevented from occurring in devices actually formed by transferring a pattern formed in a template, and manufacturing yield can be accordingly improved much more to thereby reduce manufacturing costs.

Fourth Embodiment

According to the method for inspection in the third embodiment, presence or absence of a defect on a template 100 is specified by estimating near-field light through a simulation using design data of the template 100, and by comparing a measurement result of measuring near-field light actually detected from the template 100, with a result of the simulation. In the fourth embodiment, virtual design data of a template 100 is derived from a measurement result of measuring near-field light which is actually detected in the front surface side of the template 100. Presence or absence of a defect on the template 100 is specified by comparing true design data of the template 100 with the virtual design data of the template 100.

A method for inspecting a nano-imprint template, according to the fourth embodiment of the invention, will now be described with reference to FIG. 4. Basis of a structure and a forming method is the same as those of the embodiments described above. Therefore, matters, which have been described in the above embodiments and are derivable easily from the embodiments, will be omitted from descriptions given below.

As illustrated in FIG. 4, a template 100 is set on and fixed to a jig unit 101. Further, light is generated by a light source unit 102 and is irradiated onto the template 100 through a polarizing plate 103 from the back surface side of the template 100.

Next, an xyz control unit 108 adjusts a probe 104 in the Z-direction to come close to the front surface of the template 100, and moves the probe 104 in the X- and Y-directions along the surface of the template 100. As the probe 104 is moved close to a region where the near-field light is generated, a top end of the probe 104 generates scattered light to become a near-field light signal. Further, the near-field light signal is amplified by a photomultiplier tube 105 connected to the probe 104, and is detected by a detector 106.

Further, a PC 107 derives a relationship between intensity of the near-field light and position of the template, based on the near-field light signal detected by the detector 106. In this manner, intensity distribution of near-field light generated near the surface of the template 100 is obtained.

The PC 107 also performs, in advance, near-field light measurement simulations supposing templates containing various defects by using design data of the template 100. Simulation results thereof are accumulated in a database. Thereafter, virtual design data of the template 100 is derived, based on intensity distribution of detected near-field light and the simulation results stored in the PC 107.

Further, the PC 107 compares true design data of the template 100 obtained from pattern design data 109, with the virtual design data of the template 100.

The true design data of the template 100 and the virtual design data of the template 100 are compared with each other. If there is not particularly a difference therebetween, the template 100 is determined not to be defective. Otherwise, if there is a difference between the true design data of the template 100 and the virtual design data of the template 100 which are thus compared with each other, the template 100 is determined to be defective.

If the template 100 is determined to be defective or if a pattern is determined to be clogged with resist, the template 100 is cleaned. Otherwise, if damage is found in the template, the template 100 is discarded.

In the fourth embodiment described above, simulations are performed in advance with use of the template 100, and virtual intensity distribution of near-field light is accumulated in a database. Further, as in the first embodiment described above, near-field light generated in the front surface side of the template 100 is measured. Further, intensity distribution of the near-field light is derived based on detected information. Based on the derived intensity distribution of the near-field light and the intensity distribution of near-field light accumulated in the database, virtual design data of the template 100 is derived. Further, presence or absence of a defect on a template, the type of the defect, and the portion having the defect can be accurately determined by comparing the virtual design data of the template 100 with true design data used for actually forming the template 100. Even for a template having a pattern of nanometer order whose pitch is less than a wavelength of light, presence or absence of a defect, the portion having the defect, and the type of the defect can be accurately specified by referring to near-field light, as in the embodiments described above. As a result, defects can be prevented from occurring in devices actually formed by transferring a pattern formed in a template, and manufacturing yield can be accordingly improved much more to thereby reduce manufacturing costs.

In each of the embodiments described above, the template 100 comprises a L/S pattern. However, the same effects as described above can be obtained from a configuration in which the template 100 comprises no L/S pattern.

Also in each of the embodiments described above, the PC 107 has been described as a part of the device 1 for inspecting a nano-imprint template. However, the PC 107 need not always be a part of the device 1 for inspection but may be configured externally.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for inspecting a nano-imprint template, comprising:
    irradiating light onto a template for nano-imprinting from a back surface side of the template, the template having a front surface where a pattern is formed;
    detecting near-field light which is generated near the front surface of the template by the irradiation of the light; and
    performing an inspection of the template on the basis of the detected near-field light,
    wherein the inspection of the template is performed by comparing the near-field light detected for the template after performing a pattern transfer process, with near-field light which is generated near the surface of the template by irradiating light onto the template from the back surface side of the template before performing the pattern transfer process.

2. A method for inspecting a nano-imprint template, comprising:
    irradiating light onto a template for nano-imprinting from a back surface side of the template, the template having a front surface where a pattern is formed;
    detecting near-field light which is generated near the front surface of the template by the irradiation of the light; and
    performing an inspection of the template on the basis of the detected near-field light,
    wherein the inspection of the template is performed by comparing the detected near-field light with near-field light derived from a simulation using design data of the template.

3. The method according to claim 2, wherein intensity distribution of near-field light when the pattern formed in the template is clogged with a substance and intensity distribution of near-field light when the pattern formed in the template is defective are derived in advance through the simulation.

4. The method according to claim 3, wherein the template is cleaned if the pattern formed in the template is clogged with a substance by comparing the detected near-field light with near-field light derived from the simulation using the design data of the template.

5. The method according to claim 3, wherein the template is discarded if the pattern formed in the template is determined to be defective by comparing the detected near-field light with near-field light derived from the simulation using the design data of the template.

6. A method for inspecting a nano-imprint template, comprising:
    irradiating light onto a template for nano-imprinting from a back surface side of the template, the template having a front surface where a pattern is formed;
    detecting near-field light which is generated near the front surface of the template by the irradiation of the light; and
    performing an inspection of the template on the basis of the detected near-field light,
    wherein virtual design data of the template based on the detected near-field light is derived, and true design data of the template is compared with the virtual design data of the template.

7. The method according to claim 6, wherein intensity distribution of near-field light when the pattern formed in the template is clogged with a substance and intensity distribution of near-field light when the pattern formed in the template is defective are derived in advance through the simulation and are accumulated in a database.

* * * * *